United States Patent
Takahashi et al.

(10) Patent No.: US 7,591,200 B2
(45) Date of Patent: Sep. 22, 2009

(54) METHOD OF DETECTING HIGH-CONCENTRATION REGION DIRECTION OF POLLUTANT IN SOIL

(75) Inventors: Yasuo Takahashi, Tokyo (JP); Shigekazu Shimizu, Kitaadachi-gun (JP); Naoya Ichimura, Uji (JP); Yasuhisa Fujii, Kyoto (JP); Tokugen Yasuda, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 694 days.

(21) Appl. No.: 11/255,938

(22) Filed: Oct. 24, 2005

(65) Prior Publication Data
US 2006/0090539 A1    May 4, 2006

(30) Foreign Application Priority Data
Oct. 29, 2004  (JP)  ............................. 2004-315845
Jul. 22, 2005  (JP)  ............................. 2005-212918

(51) Int. Cl.
*G01N 15/08*  (2006.01)
(52) U.S. Cl. ................... 73/866; 73/38; 73/436
(58) Field of Classification Search ............ 73/38, 73/153.05, 152.41, 64.47
See application file for complete search history.

(56) References Cited

U.S. PATENT DOCUMENTS

| | | | | |
|---|---|---|---|---|
| 2,330,829 | A | * | 10/1943 | Lundberg et al. ........... 250/255 |
| 5,049,808 | A | | 9/1991 | Okahata .................... 324/71.1 |
| 6,405,135 | B1 | * | 6/2002 | Adriany et al. .................. 702/5 |
| 6,977,506 | B2 | | 12/2005 | Noda et al. .................. 324/464 |
| 7,034,539 | B2 | * | 4/2006 | Ueda et al. .................. 324/357 |
| 2002/0167412 | A1 | * | 11/2002 | Cuming ..................... 73/64.47 |

FOREIGN PATENT DOCUMENTS

| JP | 2759683 | 3/1998 |
|---|---|---|
| JP | 3292866 | 4/2002 |
| JP | 3443632 | 6/2003 |
| JP | 2004-108913 | 4/2004 |

OTHER PUBLICATIONS

Hiromi Sakata et al., "Chemical Source Localization Using Underwater Compass System," Data of the Research Conference on a Chemical Sensor by the Institute of Electrical Engineers, vol. CHS-03-72, No. 56-86, pp. 75-80 (2003) (with English Abstract).
Hiromi Sakata et al., "Study on Underwater Chemical Compass Mimicking Crayfish Behavior," Convention Record of the Institute of Electronics, Information and Communication Engineers, vol. 2004, Electronics 2, p. 151 (with English Translation).

* cited by examiner

*Primary Examiner*—Hezron Williams
*Assistant Examiner*—Alex Devito
(74) *Attorney, Agent, or Firm*—Fitzpatrick, Cella, Harper & Scinto

(57) ABSTRACT

A recovery phenomenon in which the concentration of a compound to be measured in soil increases again after reducing the concentration is utilized for changing the distribution state of the compound to be measured in soil, whereby the direction of the high-concentration region of the compound to be measured in soil can be detected.

2 Claims, 7 Drawing Sheets

AZIMUTH DETECTION EXPERIMENT
DISTANCE: 3cm

METHOD OF DETECTING HIGH-CONCENTRATION REGION DIRECTION OF POLLUTANT IN SOIL

BACKGROUND OF THE INVENTION

1. Field of the Invention

The present invention relates to a method of grasping the distribution state of a compound in soil. More specifically, the present invention relates to a method of detecting the high-concentration region direction of a compound in soil using a frequency-converting element or the like. In this specification, the term "soil" includes all components composed of a solid, a liquid and a gas, for forming the earth and groundwater.

2. Related Background Art

There are prior arts such as "Search for chemical substance source by means of submerged compass system" and "Research on compass for searching chemical substance source in water imitating crayfish" (see "Data of the research conference on a chemical sensor by the Institute of Electrical Engineers" VOL. CHS-03, NO. 56-86; PAGE. 75-80; (20031128-20031129), Hiroshi Sakata, Seigo Ito, Hiroshi Ishida, Toyosaka Moriizumi, (Tokyo Institute of Technology), "Convention record of the Institute of Electronics, Information and Communication Engineers" VOL. 2004, Electronics 2; PAGE. 151; (20040308), Hiroshi Sakata, Hiroshi Ishida, Toyosaka Moriizumi, (Tokyo Institute of Technology) (hereinafter, referred to as "Document 1" and "Document 2", respectively)).

Hereinafter, a conventional method of detecting the direction of the position of a pollutant will be described with reference to Documents 1 and 2.

Document 1 discloses "A compass for searching an odor source in water capable of detecting a chemical substance by actively sucking water around the substance was developed. A slit was arranged immediately before a sensor electrode arranged at the inlet of a circular pipe to enable a sucked chemical substance to be surely captured by the sensor electrode. In addition, it has been confirmed that the range of directions to be sucked by each slit can be controlled by changing the number of slits and the width of each slit. A submerged compass having 4 sensor electrodes was produced. As a result, observing which sensor responds allows one to judge whether a substance source is present in the range of the forward direction ±20°, or left or right region except for the range. The compass system was attached to a linear actuator to perform an experiment for searching a chemical substance source in still water in a water tank. As a result, the search was successful at a high probability."

Document 2 discloses "A crayfish can attract not only an odor isotropically from its surrounding but also a flow intensively from one of its right and left sides by using its fan-like appendages called gnathopods. The present document realized a function of sucking from only a specific direction, by imitating the gnathopods of a crayfish to separately use right and left gnathopod structures. The use of a gnathopod structure makes it possible to realize a system for searching the presence or absence of a source by efficiently collecting signals from various places around the system."

Document 1 describes a system for detecting a chemical substance by actively sucking the substance through a slit. When the system is applied to the search for the direction of a volatile chlorinated organic compound (VOC) in soil, differences in the rate of a sucking stream and the rate of a sucking wind occur owing to differences in granularity and porosity in the soil other than the slit, to thereby destabilize a concentration signal. In addition, in such system as described in Document 2, suction causes turbulence to make a concentration signal more unstable than that in the present invention. As described above, a suction system destabilizes a concentration signal and deteriorates a detection lower limit. Therefore, such system is not suitable for detecting a VOC at an extremely low concentration and for detecting a direction of interest. In addition, the system described in Document 2 does not express a suction function in a condition like soil where the amount of dirt is larger than that of water because the wing of a gnathopod structure does not move in such condition, although the system can express the suction function in water.

Investigation into the distribution of pollution by a chlorinated organic compound such as trichloroethylene that pollutes soil has been conducted by detecting and measuring a volatile chlorinated organic compound by means of a detecting tube in a boring hole at a certain interval or in a shallow excavated hole. However, tracking down a region where a high concentration of chlorinated organic compound is present is extremely difficult. A chlorinated organic compound that has polluted soil is dissolved into groundwater and soil water to diffuse, and is vaporized to diffuse and move in the soil. The movement causes the compound to distribute in the soil while forming a certain concentration gradient in the soil.

A large number of methods each involving analyzing a gas sample collected from soil by means of an analyzer such as a gas chromatograph have been adopted for detecting a chlorinated organic compound such as trichloroethylene. In addition, Japanese Patent Application Laid-Open No. 2004-108913 discloses a gas measurement method including: subjecting a gas to be measured to oxidation and reduction decomposition in a reaction tube to transform the gas to be measured into a decomposition product; and detecting the gas by means of a chemical reaction between the decomposition product and a quartz resonator electrode material or adsorption property between them. However, the method is not intended for detecting a distribution. In addition, Japanese Patent No. 3443632 discloses, as a technique for direct detection, a method of measuring a gaseous chlorinated organic compound by means of a quartz resonator having an electrode to which lipid is applied. However, the method is intended for detecting the concentration of a gaseous chlorinated organic compound, and it is not possible to detect the distribution state of a chlorinated organic compound in soil in soil water, ground water, or the like.

Japanese Patent No. 2759683 discloses the constitution of a quartz resonator for detecting a compound in water by means of a quartz vibrating element. Here, a material for adsorbing or absorbing the compound in water is applied to one surface of one electrode of the quartz resonator, and one surface of the other electrode of the quartz resonator is coated with an electrically insulating jacket so that the electrode is out of contact with water and is in contact with the air.

The above shape has a large jacket with which the quartz resonator is coated, and involves the difficulty in grasping a change in distribution of the concentration of a VOC.

Japanese Patent No. 3292866 discloses a method of detecting the flow of a gas or an odor as a gas. The method involves: arranging a large number of sensors for detecting a gas on a plane with a spatial spread; and grasping the flow of a gas or odor upon response by each sensor element. However, if it is assumed that the method is used for measurement in soil, the sensors must be installed in a limited well or excavated hole. Therefore, it is difficult to detect the flow and direction of a gas when it is difficult to arrange the sensors widely and two-dimensionally or three-dimensionally.

SUMMARY OF THE INVENTION

The present invention has been made in order to solve the above-described problems of the prior art, and an object of the present invention is to provide a method of detecting the high-concentration region direction of a compound to be measured in soil up to an extremely low-concentration region as compared to a conventional method.

Another object of the present invention is to provide a method of detecting a direction of a high-concentration region of a compound to be measured in soil, including utilizing a difference in diffusion change of a concentration of the compound to be measured in soil from a high-concentration region and a low-concentration region in a recovery phenomenon in which a concentration of the compound increases again after reducing the concentration.

In the present method, it is preferable that the compound to be measured is a chlorinated organic compound such as trichloroethylene or tetrachloroethylene.

In the present method, it is preferable that the detection is carried out using a frequency-converting element.

In the present method, it is preferable that the frequency-converting element includes an electrode having one surface coated with a material for adsorbing the compound and other surface coated with an electrically insulating material.

In the present method, it is preferable that the concentration of the compound to be measured in a liquid phase or a gas phase in soil is reduced by jetting a liquid or a gas to the soil.

In the present method, it is preferable that the concentration of the compound to be measured in a liquid or a gas phase in soil is reduced out by removal or decomposition of the compound.

The present invention utilizes, as means for changing the distribution state of a compound to be measured in a liquid phase or in a vapor phase in soil, a recovery phenomenon in which the concentration of a compound to be measured at a point of measurement increases again after the concentration has been reduced. The present invention provides a method of detecting the high-concentration region direction of a compound to be measured in soil, including utilizing the phenomenon to measure differences in a compound concentration and various physical properties related thereto due to a difference in diffusion change from a high-concentration region and a low-concentration region.

According to the present invention, there is provided a method of easily detecting the direction in which a chemical substance in soil is distributed at a high concentration with high efficiency and high accuracy in detecting the distribution position and distribution region of the chemical substance in soil. The method has effects on not only an azimuth such as east, west, south or north but also a direction such as a vertical direction or an oblique direction. Examples of soil include soil present on the earth and soil present on the ground as a result of excavation, and the methods has an effect on each such soil.

Other features and advantages of the present invention will be apparent from the following description taken in conjunction with the accompanying drawings.

DESCRIPTION OF THE PREFERRED EMBODIMENTS

Figure 1:
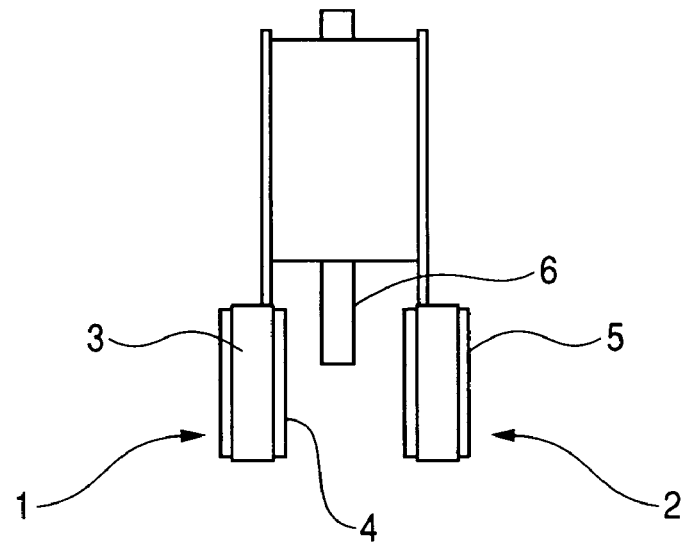
FIG. 1 is a schematic view showing the arrangement structure of a quartz resonator.

As detection means in the present invention, a frequency-converting element can be used. But elements other than the frequency-changing element can be also used, and examples thereof include conventional detection means such as surface acoustic wave element type, semiconductor type, optical type, chromatography type, electrical resistance type, and mass spectrometry type means.

Therefore, a substance to be detected by the method of the present invention is not limited to a substance to be detected by a frequency-converting element. That is, the substances and the like to be detected by the method of the present invention can include chemical substances that can be detected by conventional detection means and all various physical and electrical properties related to the chemical substances. That is, the object to be detected include a hydrogen ion concentration, a temperature, and an electric conductivity. Not only the case where a hydrogen ion concentration, a temperature, and an electric conductivity are related to the chemical substances themselves but also the case where they are related to the decomposition products, decomposition reaction heat, and the like of the chemical substances is also included in the present invention.

A substance used for coating which an electrode of the frequency-converting element in the present invention is not limited as long as it can adsorb or absorb a compound to be measured.

In the present invention, a recovery phenomenon in which the concentration of a compound to be measured in soil at a point of measurement increases again after the concentration has been reduced may be induced by any method. The any method includes, as a removal method, an injection-type removal method involving injecting water, air or the like having a low concentration of a compound to be measured, and further a suction-type removal method, an absorbent-type removal method, an adsorbent-type removal method, and a substitution-type removal method, and as a decomposition method, a ultraviolet degradation method, a thermal decomposition method, a chemical decomposition method, and a biological decomposition method. The removal method, the decomposition method or the like may be used in combination. As described above, a phenomenon is utilized in which, after a low-concentration region has been formed around a point of measurement, a difference in concentration between directions is larger than that prior to removal, decomposition or the like during or after re-diffusion. Even in the case where detection means other than a frequency-changing element is used, a method suitable for each detection means is desirably applied after such phenomenon has been induced on the basis of the same principle. Examples of such means include: various sensors each having multiple detection points or detection surfaces; detection means having multiple diffusion introduction ports; and detection means with its sampling direction of a detection direction made variable.

The ground may be subjected to a treatment such as heating for the purpose of promoting the recovery phenomenon. Also, the ground may be perforated with a cave hole or may be provided with a barrier for preventing mixing for each direction for the purpose of improving the direction accuracy of the recovery phenomenon.

The present invention will be described in more detail by way of the following Examples.

EXAMPLE 1

A resonance frequency was applied to a quartz resonator having a resonance frequency of 9 MHz (electrode diameter: 5 mm), and was measured with a frequency counter. In the quartz resonator, one surface of one electrode of the quartz resonator was coated with a vinyl resin for electrical insulation and one surface of the other electrode of the quartz resonator was coated with polystyrene to serve as a material for adsorbing trichloroethylene. As shown in FIG. 1, two quartz resonators each having the coated electrode were arranged in such a manner that the electrode surfaces coated with polystyrene would be opposite to each other and the central lines of the two quartz resonators would deviate from each other by 5 mm. In FIG. 1, reference numeral 1 denotes a sensor (1); 2, a sensor (2); 3, a quartz resonator; 4, an adsorbing material; 5, insulating coating; and 6, a water injection pipe.

Figure 2:
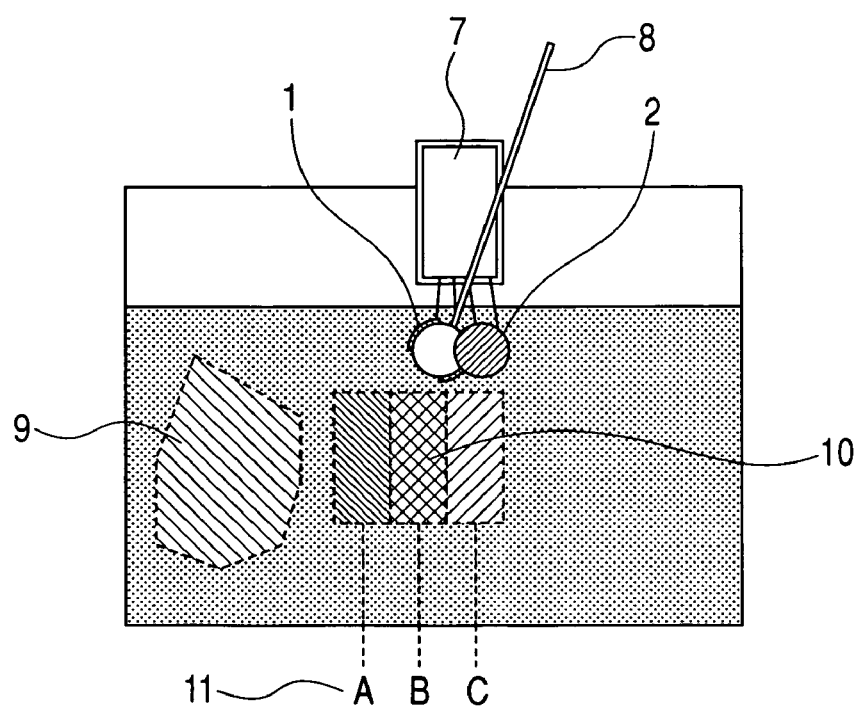
FIG. 2 is a schematic view showing the constitution of an apparatus for a soil tank experiment.

FIG. 2 shows the constitution of an experimental apparatus in a small soil tank. In FIG. 2, a part where the above two quartz resonators are combined is represented as a sensing unit. 5 ml of a 700-ppm VOC solution (trichloroethylene) were injected into a small soil tank (containing 320 g of soil and 60 ml of water), and trichloroethylene was diffused in the soil. Then, a quartz resonator part of the sensing unit was inserted into the soil to perform measurement. In FIG. 2, reference numeral 1 denotes a sensor (1); 2, a sensor (2); 7, a sensor unit; 8, injected water for distorting a concentration gradient; 9, an injected VOC solution; 10, a VOC concentration gradient; and 11, a sensor position.

Detection at a distance of each of 3 cm (position A in FIG. 2), 4 cm (position B in FIG. 2), and 5 cm (position C in FIG. 2) from a pollution source was investigated.

Data on the resonance frequency of a quartz resonator was acquired, and then 1 ml of water was injected between the two quartz resonators to measure the resonance frequency of each of the two quartz resonators.

Figure 3:
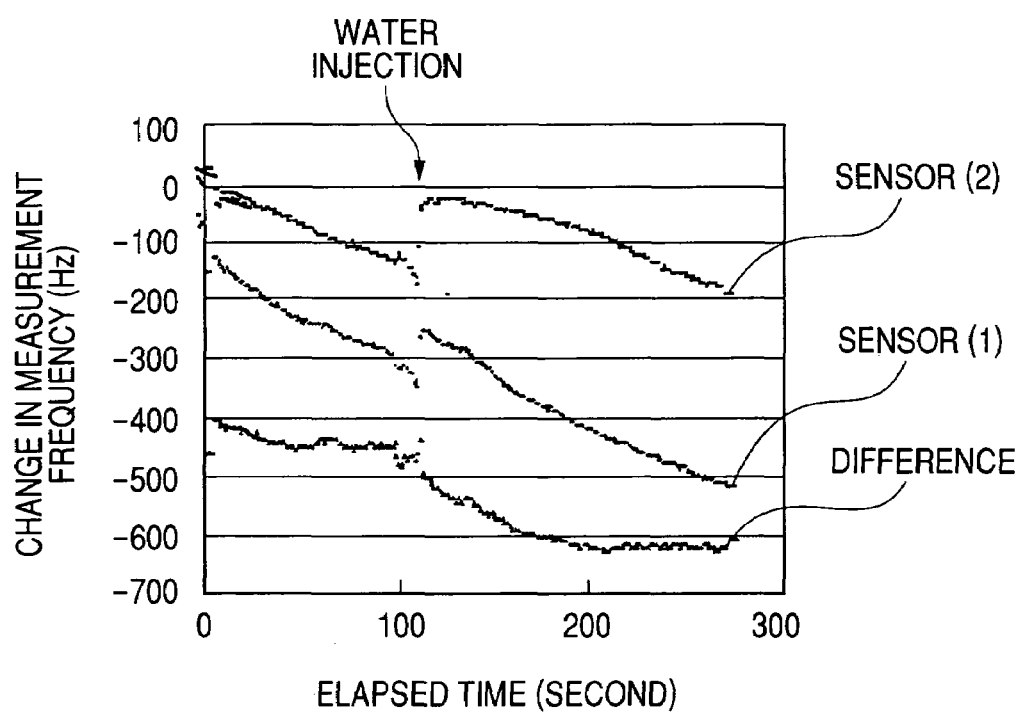
FIG. 3 is a graph showing the measured results of an azimuth detection experiment (distance: 3 cm).
Figure 4:
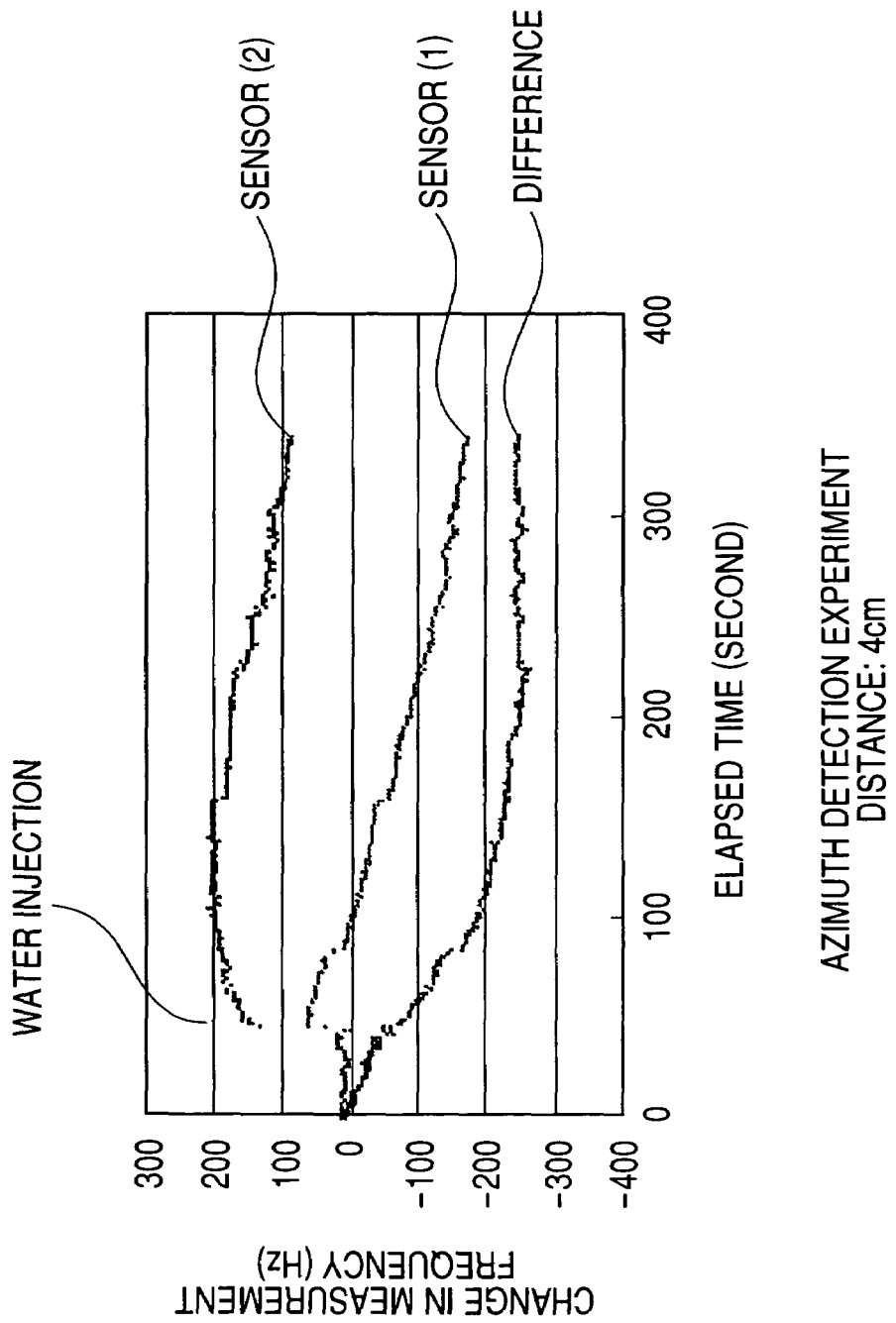
FIG. 4 is a graph showing the measured results of an azimuth detection experiment (distance: 4 cm).
Figure 5:
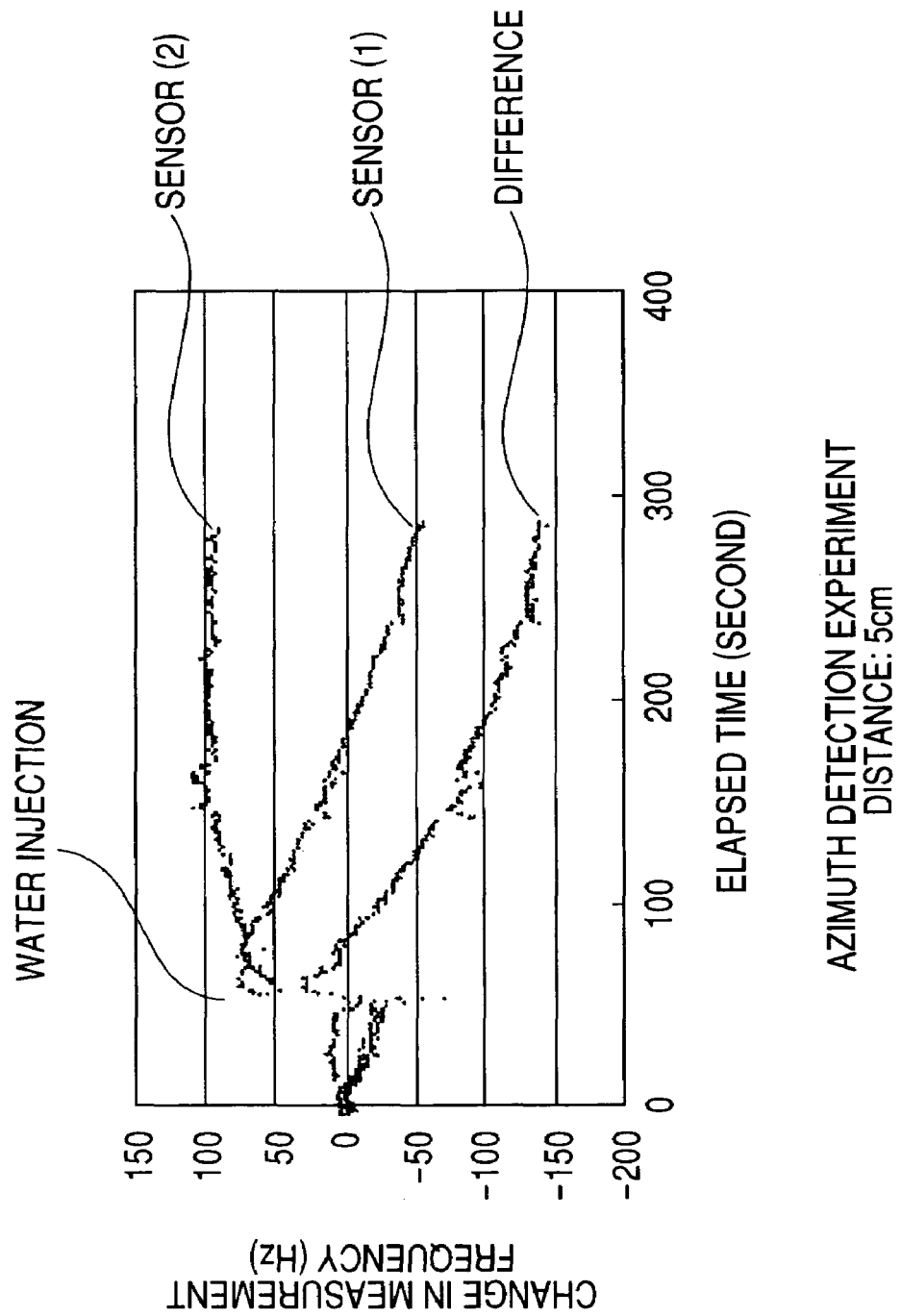
FIG. 5 is a graph showing the measured results of an azimuth detection experiment (distance: 5 cm).

Out of the two quartz resonators, a quartz resonator on the side of the VOC pollution source was represented as the sensor (1) and the other quartz resonator was represented as the sensor (2). FIG. 3 shows the measured results at a distance of 3 cm. FIG. 4 shows the measured results at a distance of 4 cm. FIG. 5 shows the measured results at a distance of 5 cm.

In FIG. 3, analysis of the behavior of a change in resonance frequency of each of the two quartz resonators reveals that the resonance frequency of the quartz resonator on the side of a higher concentration returns to the frequency changing state before injection of water faster than the frequency of the quartz resonator on the side of a lower concentration. It has been confirmed that the detection of the difference in behavior between the two quartz resonators enables the azimuth in which soil is polluted at a high concentration to be detected. Similar behavior was observed in each of FIGS. 4 and 5.

As shown in FIGS. 3, 4 and 5, the method of the present invention allows the azimuth of a VOC pollution position in soil to be detected.

Of course, detection can be performed by subjecting a quartz resonator to an electrical insulating treatment except for that disclosed in this example or by changing an interval distance between quartz resonators.

EXAMPLE 2

Figure 6:
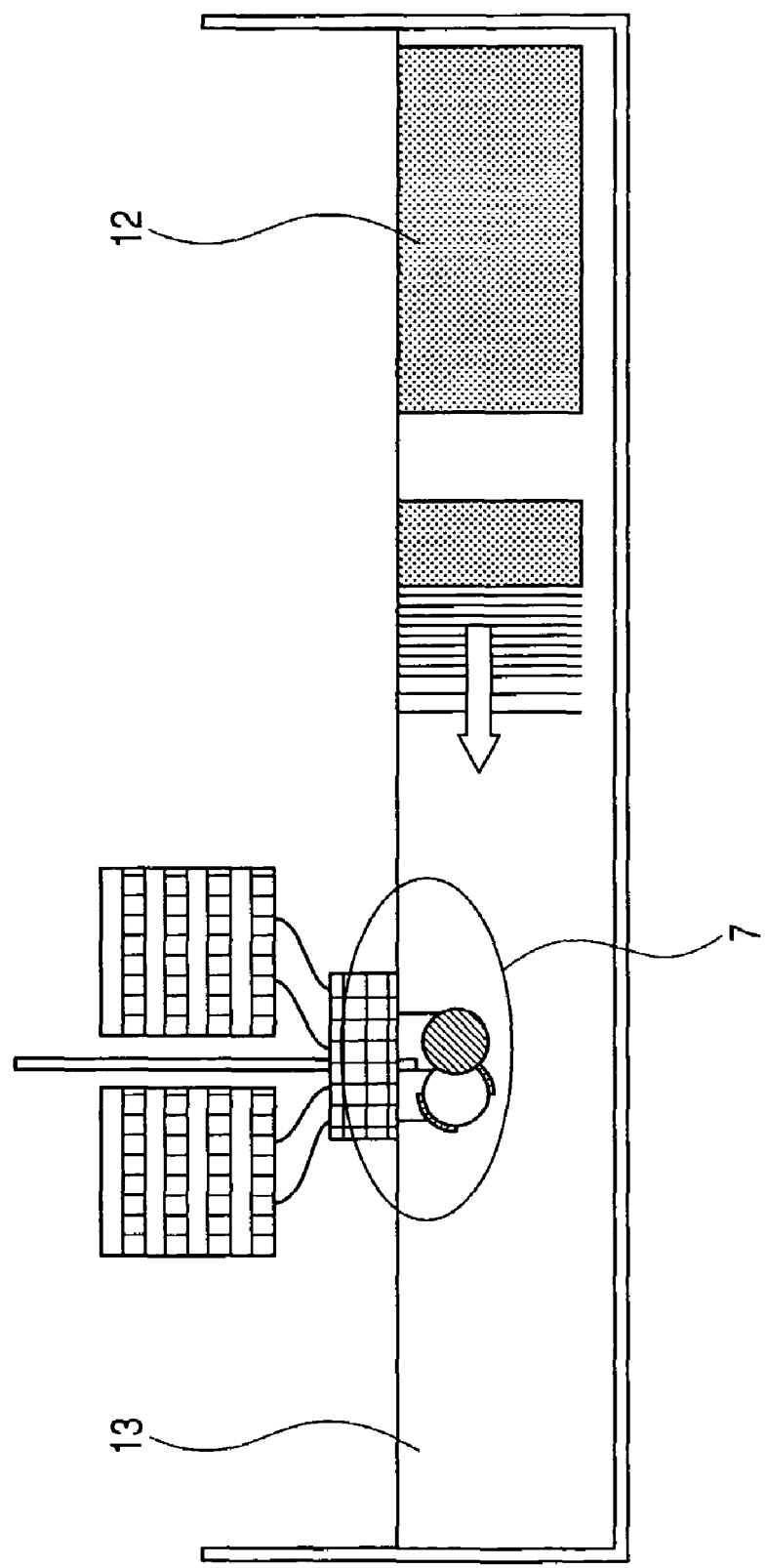
FIG. 6 is a view showing the constitution of a model used in Examples.
Figure 7:
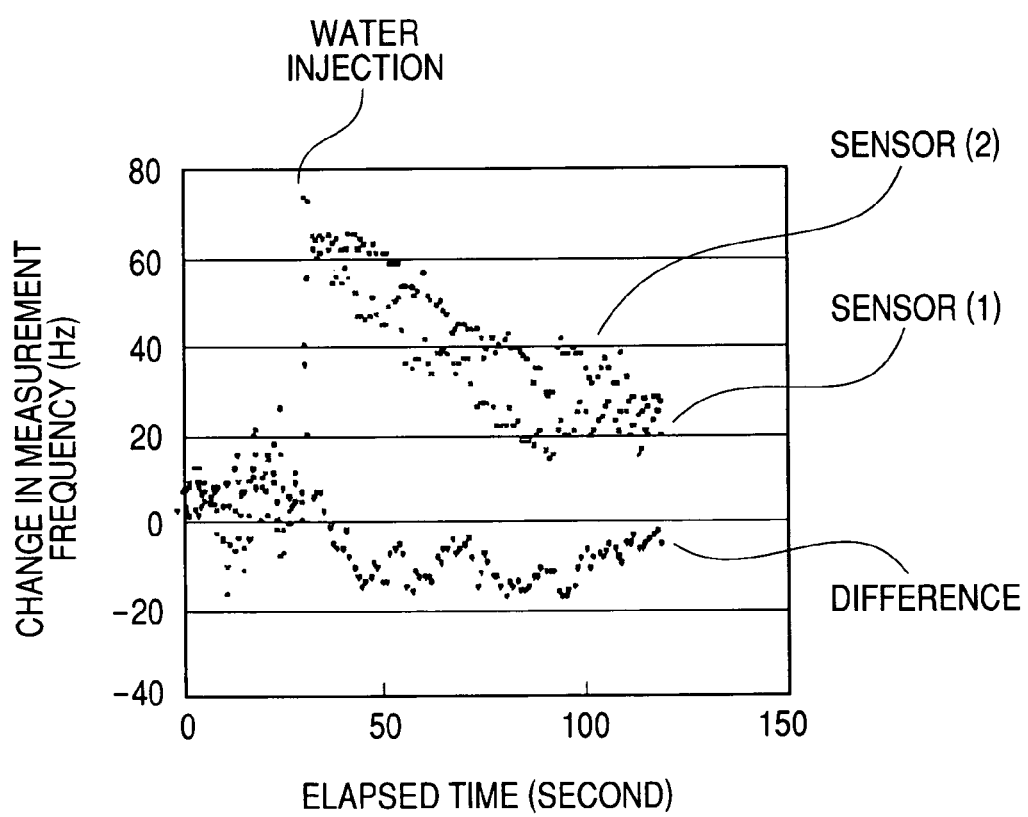
FIG. 7 is a graph showing the measured results of an azimuth detection experiment (distance 7 cm).

The sensing unit shown in Example 1 was used. Soil (4 kg of mountain gravel) was fed into a hollow tray. 200 ml of an aqueous solution of trichloroethylene (700 ppm) as a pollution source were added. An experiment for detecting a pollution azimuth in a pollution model produced by adding 600 ml of water (tap water) to the side opposite to the contamination source was conducted. FIG. 6 shows the constitution of the model used in this example. FIG. 7 shows the measured results at a distance of 7 cm from the pollution source. A difference in behavior between two quartz resonators was detected even in the case where the amount of soil was increased to be about 10 times as large as that in Example 1, the amount of trichloroethylene was increased to be about 100 times as large as that in Example 1, and the distance from the pollution source was extended to 7 cm. This detection showed that the azimuth polluted at a high concentration in soil was on the side of the sensor (1). In FIG. 6, reference numeral 7 denotes a sensor unit; 12, a VOC pollution source; and 13, 4 kg of soil.

EXAMPLE 3

Figure 8:
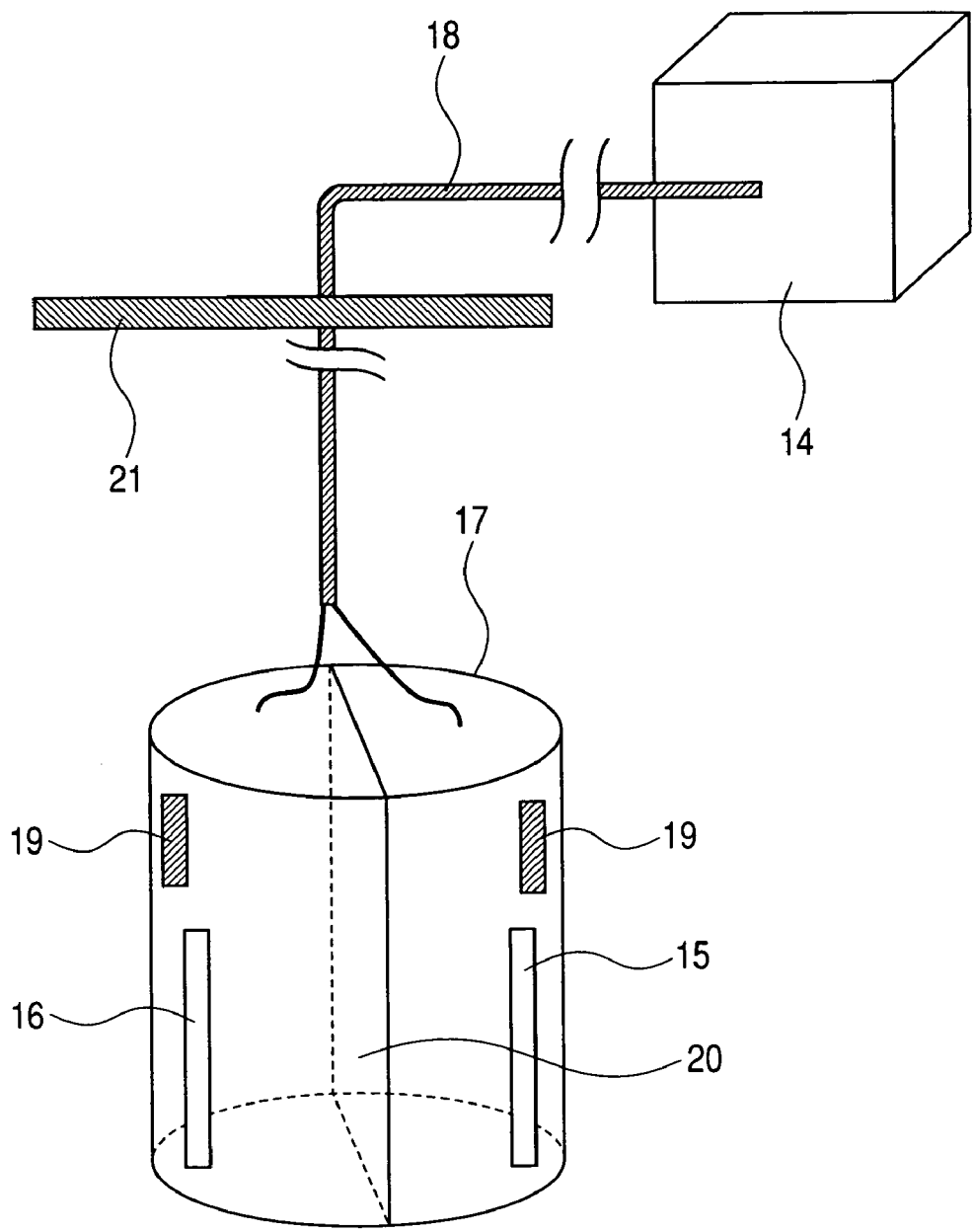
FIG. 8 is a schematic view showing an example of a sampling point of a detection apparatus.

FIG. 8 shows an example of a sampling equipment for the case where the concentration is reduced by decomposition. A trichloroethylene concentration was reduced by ultraviolet degradation. Turning an ultraviolet lamp off resulted in the recovery of a trichloroethylene concentration in a pipe partitioned by a barrier into two chambers. A difference in trichloroethylene concentration between the two chambers was able to be detected. The detection showed that the azimuth polluted at a high concentration in soil was on the side of a diffusion introduction slit (1). In FIG. 8, reference numeral 14 denotes a detection apparatus: gas chromatograph (schematic view) (gas suction function included); 15, the diffusion introduction slit (1) (enlarged view); 16, a diffusion introduction slit (2) (enlarged view); 17, a pipe for forming a slit for each direction (enlarged view); 18, a piping system for introduction to the detection apparatus after separate sampling from two chambers (schematic view); 19, an ultraviolet lamp; 20, a barrier; and 21, the ground.

As described above, according to the present invention, there is provided a method of detecting a direction of with which the high-concentration region of a compound to be measured distributing in soil can be detected.

Those to be detected by the present invention can include all chemical substances for each of which detection means is available and various physical properties related to the chemical substances.

This application claims priority from Japanese Patent Applications No. 2004-315845 filed on Oct. 29, 2004 and No. 2005-212918 filed on Jul. 22, 2005, which are hereby incorporated by reference herein.

What is claimed is:

1. A method of detecting a direction of a high-concentration region of a compound to be measured in soil, the method comprising:

reducing a concentration of the compound in a portion of the soil; and then detecting within the portion a difference in a change of the concentration of the compound caused by diffusion of the compound from regions adjacent to the portion, wherein the detecting is carried out using a frequency-converting element comprising one electrode having a surface coated with a material for adsorbing the compound and another electrode having a surface coated with an electrically insulating material.

2. A method of detecting a direction of a high-concentration region of a compound to be measured in soil, the method comprising:

reducing a concentration of the compound in a portion of the soil; and then detecting within the portion a difference in a change of the concentration of the compound caused by diffusion of the compound from regions adjacent to the portion, wherein the compound is in a liquid or gas phase in the soil, and wherein the concentration of the compound is reduced by decomposing the compound in the soil.

* * * * *